United States Patent [19]

Chang et al.

[11] Patent Number: 4,761,174

[45] Date of Patent: Aug. 2, 1988

[54] TRIAZOLIN-5-ONE HERBICIDES

[75] Inventors: Jun H. Chang, Princeton Junction; John W. Lyga, Somerset Co., both of N.J.

[73] Assignee: FMC Corporation, Philadelphia, Pa.

[21] Appl. No.: 104,598

[22] Filed: Sep. 30, 1987

Related U.S. Application Data

[63] Continuation-in-part of Ser. No. 38,169, Apr. 14, 1987, abandoned, which is a continuation of Ser. No. 3,450, Jan. 15, 1987, abandoned.

[51] Int. Cl.$^4$ .................. A01N 43/84; C07D 413/04
[52] U.S. Cl. ........................................... 71/92; 71/88; 544/105
[58] Field of Search ............................. 544/105; 71/92

[56] References Cited

U.S. PATENT DOCUMENTS

| | | | |
|---|---|---|---|
| 4,139,364 | 2/1979 | Wolf | 544/105 X |
| 4,619,687 | 10/1986 | Haga et al. | 544/105 X |
| 4,640,707 | 2/1987 | Nagano et al. | 544/105 X |

FOREIGN PATENT DOCUMENTS 149571 1/1984 Japan .
85/04307 10/1985 PCT Int'l Appl. .
2162511 2/1986 United Kingdom .

Primary Examiner—Richard L. Raymond
Attorney, Agent, or Firm—Robert M. Kennedy; H. Robinson Ertelt; Abner Sheffer

[57] ABSTRACT

Herbicidal compounds of the formula

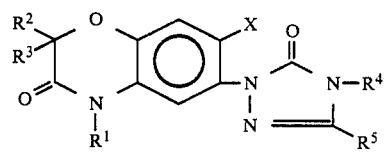

in which
$R^1$ is H, alkyl, alkenyl, alkynyl, haloalkyl, haloalkenyl, haloalkynyl, alkoxyalkyl, alkoxyalkoxyalkyl, alkylsulfonyl, aralkyl, alkylthioalkyl, hydroxy or alkoxy;
$R^2$ and $R^3$ are independently H or alkyl;
X is H, Cl or F;
$R^4$ is alkyl, haloalkyl, alkenyl or alkynyl;
$R^5$ is alkyl or haloalkyl.

10 Claims, No Drawings

TRIAZOLIN-5-ONE HERBICIDES

This application is a continuation-in-part, of application Ser. No. 038,169, now abandoned, filed 4/14/87, which is a continuation of application Ser. No. 003,450, filed 1-15-87, now abandoned.

This invention relates to triazolinones of the following formula I and their use as herbicides:

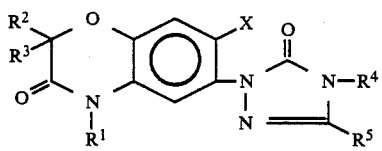

Formula I in which $R^1$ is:
H;
alkyl, e.g. methyl, ethyl or propyl;
alkenyl, e.g. allyl or methyallyl;
alkynyl, e.g. propynyl or methylpropynyl;
haloalkyl, e.g. 3-chloropropyl;
haloalkenyl, e.g. 2-chloropropenyl or 2,3-dichloropropenyl;
haloalkynyl, e.g. 3-bromopropynyl;
alkoxyalkyl, e.g. methoxymethyl or ethoxymethyl;
alkoxyalkoxyalkyl, e.g. ethoxymethoxymethyl;
alkylsulfonyl, e.g. methylsulfonyl or ethylsulfonyl;
aralkyl, e.g. benzyl;
cycloalkyl, e.g. cyclopropylmethyl;
alkylthioalkyl, e.g. methylthiomethyl;
hydroxy; or alkoxy, e.g. methoxy or ethoxy.

$R^2$ and $R^3$ are, independently
H or alkyl, e.g. methyl, preferably H.
X is H, Cl or F, preferably F.
$R^4$ is alkyl (e.g. methyl or ethyl), haloalkyl (e.g. fluoroalkyl such as $CHF_2$, $CH_2F$, $CH_2CH_2F$ or $CH_2(CH_2)_2F$), alkenyl (e.g. allyl), alkynyl (e.g. propynyl), preferably $CHF_2$.

$R^5$ is alkyl (e.g. methyl), haloalkyl (e.g. fluoroalkyl such as $CHF_2$), preferably $CH_3$. $R^5$ may also be H.

The compounds in which $R^1$ is H, while having herbicidal properties at high application rates, are primarily useful as intermediates is producing compounds of the invention in which $R^1$ is other than H.

In each aspect of the invention it is often preferable that any alkyl, cycloalkyl, alkenyl, alkynyl or alkylene moiety (such as the hydrocarbon moiety of an alkoxy or haloalkoxy group) have less than 6 carbon atoms, e.g. 1 to 3 carbon atoms.

The compounds of this invention may be prepared by the use of steps generally described in the literature or in the following Examples or by methods analogous or similar thereto and within the skill of the art. In Example 1 below, there is formed a 1-aryl-$\Delta^2$-1,2,4-triazolin-5-one from an aniline in known manner (such as in a manner taught in published International Application No. WO 86/02642 published May 9, 1986, said Application incorporated herein by reference). The aryltriazolinone is treated to introduce a carboalkoxymethoxy or similar group at the 4-position of the benzene ring and a nitro group at the 5-position to form a compound of the formula

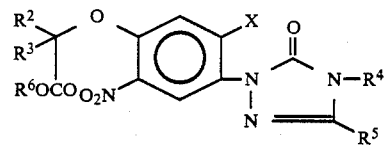

Formula II where $OR^6$ is alkoxy or a similar group which can be split out in the next steps. Then, in known manner (J. Am. Chem. Soc., 81, 94 (1959)) by treatment with iron in an acidified solvent, e.g. at an elevated temperature such as 60°-150° C., reduction of the nitro group to an amino group, followed by ring closure between said 4- and 5-positions is effected, forming a compound of the formula,

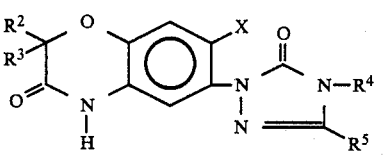

Formula III

After this an $R^1$ group is introduced, as by reaction with $R^1X^1$ (where $X^1$ is a leaving group such as a halogen), to form the final compound.

To produce compounds in which $R^1$ is hydroxy or alkoxy the reduction and ring closure step may be effected by using a milder reducing agent (such as hydrazine in the presence of rhodium on carbon) to form, during the reaction, an intermediate having a—NHOH group (instead of an—$NH_2$ group) at the 5-position of the benzene ring so that on cyclization there is formed a compound having the formula

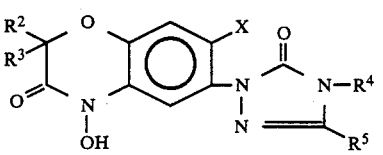

Formula IV after which that compound is treated with an appropriate alkyl halide (e.g. methyl iodide in the presence of NaH).

To produce compounds in which $R^1$ is haloalkynyl the compound in which $R^1$ is alkynyl may be reacted with the halogen (e.g. iodine or bromine) in the presence of a base (e.g. NaOH or KOH); also a catalyst such as benzyltriethylammonium bromide or chloride or tetrabutylammonium bromide may be present.

Example 2, below, illustrates the production of compounds of Formula II starting with 2,4-difluoroaniline by converting the latter to a 1-(2,4-difluorophenyl)-$\Delta^2$-1,2,4-triazolin-5-one, then nitrating to form a compound of the formula

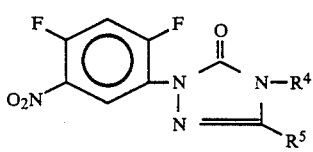

Formula V followed by replacing the F at C-4 of the phenyl moiety with —$OC(R^2)(R^3)CO_2R^6$ to form a compound of Formula II in which X is F.

The following Examples are given to illustrate this invention further. In this application all parts are by weight unless otherwise indicated. In the Examples, the term "concentrated", referring to a procedure in the process, relates to evaporating under reduced pressure in conventional manner to remove volatiles such as solvent. Also, in the Examples, the mixtures are stirred in conventional fashion and the reaction is carried out in inert atmosphere when appropriate (e.g. in the reaction involving sodium hydride).

In Example 1 the starting material is 1-(4-hydroxy-2-fluorophenyl)-3-methyl-4-difluoromethyl-$\Delta^2$-1,2,4-triazolin-5-one (m.p. 99°–101° C.) which may be produced in the manner described in Example 1 of published PCT International Application No. WO 85/01637 published Apr. 25, 1985, except that one uses 2-fluoro-4-methoxyaniline instead of the 4-chloro-2-fluoro-5-methoxyaniline of that published Example 1.

EXAMPLE 1

Step A 3.8 g of 1-(4-hydroxy-2-fluorophenyl)-3-methyl-4-difluoromethyl-$\Delta^2$-1,2,4-triazolin-5-one (0.0147 mol) was dissolved in 10 ml of concentrated $H_2SO_4$. Then a mixture of 1.3 ml of 70% $HNO_3$ and 2 ml of concentrated $H_2SO_4$ was added at about 0° C., and the resulting reaction mixture was poured into ice water, then extracted with ethyl acetate, after which the extract was concentrated to yield 4.3 g of an oil, which was then chromatographed on silica gel with a 1:1 (by volume) mixture of ethyl acetate and heptane, to yield 2.8 g of a yellow solid, 1-(4-hydroxy-2-fluoro-5-nitrophenyl)-3-methyl-4-difluoromethyl-$\Delta^2$-1,2,4-triazolin-5-one.

Step B

The product of the preceding step (2.8 g, 0.0092 mol) was dissolved in 5 ml of N,N-dimethylformamide ("DMF") and added to a suspension of 0.01 mol of NaH in 10 ml of DMF at room temperature. Then a solution of 1.14 ml of ethyl bromoacetate (0.01 mol) in 5 ml of DMF was added. The resulting reaction mixture was poured into dilute HCl and then extracted with ethyl acetate. The extract was washed with saturated aqueous $NaHCO_3$ and the resulting organic layer was concentrated to a solid; the aqueous $NaHCO_3$ layer was acidified with concentrated HCl and extracted with ethyl acetate and the resulting extract was also concentrated to a solid. The two solid concentrates were redissolved together in acetone; then 2 g of $K_2CO_3$ and 1 ml of ethyl bromoacetate were added and the mixture was heated at reflux temperature for about 20 hours. The reaction mixture was then poured onto a mixture of ice and water and then extracted with ethyl acetate, after which the extract was washed with saturated aqueous NaCl and concentrated to yield about 2 g of a solid 1-(4-carboethoxymethoxy-2-fluoro-5-nitrophenyl)-3-methyl-4-difluoromethyl-$\Delta^2$-1,2,4-triazolin-5-one.

Step C

All of the product of the previous step was dissolved in 5 ml of acetic acid and added to 2 g of iron powder in 10 ml of acetic acid at 90° C. After 1 hour of reaction the mixture was poured into water and then extracted with ethyl acetate. The extract was dried over magnesium sulfate, treated with charcoal and then concentrated to yield 1.6 g of a solid, 1-(7-fluoro-2H-1,4-benzoxazin-3(4H)-on-6-yl)-3-methyl-4-difluoromethyl-$\Delta^2$-1,2,4-triazolin-5-one.

Step D 0.86 g of the product of the preceding step (0.00274 mol) was dissolved in 5 ml of DMF and added to a suspension of 0.003 mol of NaH in 5 ml of DMF. The resulting mixture was warmed to 50° C. After 15 minutes a solution of 0.51 g of 1-iodopropane (0.003 mol) in 5 ml of DMF was added and the mixture was stirred at room temperature for an additional hour. The reaction mixture was then poured into a mixture of ice water and concentrated HCl and then extracted with ethyl acetate. The extract was dried over magnesium sulfate and concentrated to an oil which was then chromatographed on silica gel with 1:1 (by volume) ethyl acetate/heptane to yield 0.8 g of a clear yellow oil which solidified on standing, 1-[7-fluoro-4-propyl-2H-1,4-benzoxazin-3(4H)-on-6-yl]-3-methyl-4-difluoromethyl-$\Delta^2$-1,2,4-triazolin-5-one.

For each of the compounds produced in steps A–D above, the nmr was consistent with the described structure.

Instead of the iodopropane one may substitute (in step D) other reactive halides in the last step, so as to form the corresponding compounds having other $R^1$ substituents, e.g. ethyl iodide, methyl iodide, propargyl bromide, methoxymethyl bromide, methylthiomethyl chloride, benzyl bromide, ethylsulfonyl chloride, allyl bromide, and cyclopropylmethyl bromide to form, respectively, compounds 3–9, 36, and 57 of Table 1 below. Similarly, compounds in which $R^1$ is haloalkenyl may be produced by using such reactants as cis or trans 2,3-dichloropropenyl bromide or 2-chloropropenyl bromide or 3-chloropropenyl bromide or 1,2-bromopropene (for compound 56) in step D.

EXAMPLE 2

Step A 2-(2,4-difluorophenylhydrazono)propionic acid

Under a dry nitrogen atmosphere, a stirred solution of 25.8 g (0.20 mol) of 2,4-difluoroaniline in 235 ml of concentrated hydrochloric acid was cooled to −10° C. While maintaining this temperature, a solution of 13.8 g (0.20 mol) of sodium nitrite in 80 mol of water was added dropwise. After complete addition, the mixture was stirred at −10° C. for one hour. A solution of 101.5 g (0.450 mol) of tin (II) chloride dihydrate in 115 ml of concentrated hydrochloric acid was added dropwise to the cold reaction mixture. The resultant mixture was stirred for two hours, allowing the reaction temperature to rise to room temperature. Water (200 ml) was added to the mixture followed by the dropwise addition of 17.6 g (0.020 mol) of pyruvic acid in 200 ml of water. The resultant suspension was stirred vigorously for 45 minutes, and was filtered. The filter cake was dried to yield 40.4 g of 2-(2,4-difluorophenylhydrazono)propionic acid as a solid.

The nmr spectrum was consistent with the proposed structure.

Step B 1-(2,4-difluorophenyl)-3-methyl-$\Delta^2$-1,2,4-triazolin-5-one

A stirred mixture of 40.0 g (0.187 mol) of 2-(2,4-diflurorophenylhydrazono)propionic acid, 52.3 g (0.190 mol) of diphenylphosphoryl axide, and 20.2 g of triethylamine in 1,160 ml of toluene was heated at reflux for four hours. The reaction mixture was cooled and was extracted with three 350 ml portions of an aqueous, 1N sodium hydroxide solution. The basic extracts were combined and cooled to about 5° C. The combined extract was acidified with concentrated hydrochloric acid, forming a precipitate. This precipitate was collected by filtration and the filter cake was washed with cold water followed by diethyl ether. The washed filter cake was dried to yield 20.4 g of 1-(2,4-difluorophenyl)-3-methyl-$\Delta^2$-1,2,4-triazolin-5-one as a solid.

The nmr spectrum was consistent with the proposed structure.

Step C 1-(2,4-difluorophenyl)-3-methyl-4-difluoromethyl-$\Delta^2$-1,2,4-triazolin-5-one A stirred mixture of 20.3 g (0.095 mol) of 1-(2,4-difluorophenyl)-3-methyl-$\Delta^2$-1,2,4-triazolin-5-one and 16.1 g (0.050 mol) of tetra-n-butylammonium bromide in 600 ml of tetrahydrofuran: methylene chloride (1:1) was cooled in an ice bath. To the cold mixture was added 22.4 g (0.40 mol) of powdered potassium hydroxide and the mixture was stirred for 15 minutes. Chlorodifluoromethane gas was added to the reaction mixture via a submerged inlet tube for approximately 2.5 hours, keeping the reaction temperature at 25° C. The reaction was quenched by the slow addition of 800 ml of water. The organic phase was separated from the aqueous phase. The aqueous phase was extracted with ethyl acetate. The organic phases were combined and dried over anhydrous magnesium sulfate. This mixture was filtered and the filtrate was evaporated under reduced pressure to leave a solid residue. This residue was dissolved in methylene chloride and filtered through a column of silica gel. The filtrate was evaporated under reduced pressure to yield 14.0 g of a mixture containing approximately 60% 1-(2,4-difluorophenyl)-3-methyl-4-difluoromethyl-$\Delta hu 2$-1,2,4-triazolin-5-one and approximately 40% 1-(2,4-difluorophenyl)-3-methyl-5-difluoromethoxy-$\Delta hu 2$-1,2,4-triazole.

This mixture was dissolved in 140 ml of glacial acetic acid and 7.0 ml of concentrated hydrochloric acid and was heated at reflux for 16 hours. The mixture was cooled to room temperature and poured into one liter of ice-water. The aqueous mixture was extracted several times with ethyl acetate. The extracts were combined and washed with an aqueous, saturated sodium bicarbonate solution. The washed organic phase was dried over anhydrous magnesium sulfate and filtered. The filtrate was evaporated under reduced pressure to leave a solid residue. This solid was stirred in 200 ml of diethyl ether for one hour. The insoluble 1-(2,4-difluorophenyl)-3-methyl-$\Delta^2$-1,2,4-triazolin-5-one (3.4 g) was removed by filtration. The filtrate was evaporated under reduced pressure to yield 6.4 g of 1-(2,4-difluorophenyl)-3-methyl-4-difluoromethyl-$\Delta^2$-1,2,4-triazolin-5-one as a solid.

The nmr spectrum was consistent with the proposed structure.

Step D 1-(2,4-difluoro-5-nitrophenyl)-3-methyl-4-difluoromethyl-$\Delta^2$-1,2,4-triazolin-5-one The nitration of 6.3 g (0.024 mol) of 1-(2,4-difluorophenyl)-3-methyl-4-difluoromethyl-$\Delta^2$-1,2,4-triazolin-5-one with 2.3 g (0.026 mol) of nitric acid in 25 ml of sulfuric acid yielded 6.4 g of 1-(2,4-difluoro-5-nitrophenyl)-3-methyl-4-difluoromethyl-$\Delta^2$-1,2,4-triazolin-5-one as a solid.

The nmr spectrum was consistent with the proposed structure.

Step E 1-(4-carboethoxymethoxy-2-fluoro-5-nitrophenyl)-3-methyl-4-difluoromethy-$\Delta^2$-1,2,4-triazolin-5-one Under a dry nitrogen atmosphere a stirred solution of 6.4 g (0.021 mol) of 1-(2,4-difluoro-5-nitrophenyl)-3-methyl-4-difluoromethyl-$\Delta^2$-1,2,4-triazolin-5 -one and 2.2 g (0.024 mol) of methyl glycolate in 150 ml of anhydrous tetrahydrofuran was cooled to 0° C. While maintaining a reaction temperature of 0° C., sodium hydride (0.58 g, 0.024 mol) was added portion wise. The resultant mixture was stirred at 0° C. for two hours. The mixture was poured into dilute hydrochloric acid and the resultant mixture was extracted with ethyl acetate. The extract was washed with an aqueous, saturated sodium carbonate solution followed by an aqueous saturated sodium chloride solution. The washed extract was dried over anhydrous magnesium sulfate and filtered. The filtrate was evaporated under reduced pressure leaving a residue. This residue was stirred in diethyl ether, forming a solid. This solid was collected by filtration to yield 5.2 g of 1-(4-carboethoxymethoxy-2-fluoro-5-nitrophenyl)-3-methyl-4-difluoromethyl-$\Delta^2$-1,2,4-triazolin-5-one. The nmr spectrum was consistent with the proposed structure.

The herbicidal data in the following Tables 3 and 4 were obtained in the manner described in PCT published application no. WO 85/01939, previously mentioned, usually employing solutions of the herbicidal compound in 50/50 acetone/water mixtures. In those tables, the test compounds are identified by numbers which correspond to those in Table 1, "kg/ha" is kilograms per hectare, and "% C" is percent control.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable power formulations are:

| Component: | % by Wt. |
| --- | --- |
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
| --- | --- |
| Active ingredient | 53.01 |
| Blend of alkylnaphthalenesulfonate | 6.00 |

-continued

| Component: | % by Wt. |
| --- | --- |
| and polyoxyethylene ethers | |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
| --- | --- |
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
| --- | --- |
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |

|                                         | % by Wt. |
|-----------------------------------------|----------|
| Polyacrylic acid thickener              | 0.30     |
| Dodecylphenol polyethylene glycol ether | 0.50     |
| Disodium phosphate                      | 1.00     |
| Monosodium phosphate                    | 0.50     |
| Polyvinyl alcohol                       | 1.00     |
| Water                                   | 56.70    |
| Total                                   | 100.00   |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 2 of the tables below has, in greenhouse testing at pre-emergence dosages as low as about 0.015, 0.007 and 0.004 kg/ha, given good weed control with no damage to soybeans. For field use, where there are losses of herbicide, larger dosages (e.g. four times the dosage mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitrolaniline herbicides such as 2,6-dinitro-N,N-dipropyl-4-(trifluoromethyl)benzeneamine (trifluralin); and aryl urea herbicides such as N'-(3,4-dichlorophenyl)-N, N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

TABLE 1

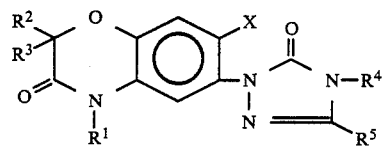

| Cmpd. No. | X  | $R^1$                                | $R^2$  | $R^3$ | $R^4$        | $R^5$   |
|-----------|----|--------------------------------------|--------|-------|--------------|---------|
| 1         | F  | H                                    | H      | H     | $CHF_2$      | $CH_3$  |
| 2         | F  | $CH_2CH_2CH_3$                       | H      | H     | $CHF_2$      | $CH_3$  |
| 3         | F  | $C_2H_5$                             | H      | H     | $CHF_2$      | $CH_3$  |
| 4         | F  | $CH_3$                               | H      | H     | $CHF_2$      | $CH_3$  |
| 5         | F  | $CH_2C{\equiv}CH$                    | H      | H     | $CHF_2$      | $CH_3$  |
| 6         | F  | $CH_2OCH_3$                          | H      | H     | $CHF_2$      | $CH_3$  |
| 7         | F  | $CH_2SCH_3$                          | H      | H     | $CHF_2$      | $CH_3$  |
| 8         | F  | $-CH_2C_6H_5$                        | H      | H     | $CHF_2$      | $CH_3$  |
| 9         | F  | $SO_2C_2H_5$                         | H      | H     | $CHF_2$      | $CH_3$  |
| 10        | F  | $SO_2CH_3$                           | H      | H     | $CHF_2$      | $CH_3$  |
| 11        | F  | $CH_2CH{=}CH_2$                      | $CH_3$ | H     | $CHF_2$      | $CH_3$  |
| 12        | F  | $CH_2OC_2H_5$                        | H      | H     | $CHF_2$      | $CH_3$  |
| 13        | Cl | $CH_2C{\equiv}CH$                    | H      | H     | $CHF_2$      | $CH_3$  |
| 14        | F  | $CH_2C{\equiv}CH$                    | H      | H     | $CH_3$       | $CHF_2$ |
| 15        | F  | $CH_2C{\equiv}CH$                    | H      | H     | $CH_2CH_2CH_2F$ | $CH_3$ |
| 16        | F  | $CH_2CH{\equiv}CH$                   | H      | H     | $CH_2F$      | $CH_3$  |
| 17        | F  | $CH_2C{\equiv}CH$                    | H      | H     | $CH_2CH{=}CH_2$ | $CH_3$ |
| 18        | F  | $CH(CH_3)_2$                         | H      | H     | $CHF_2$      | $CH_3$  |
| 19        | F  | $CH_2F$                              | H      | H     | $CHF_2$      | $CH_3$  |
| 20        | F  | $CH_2CH_2F$                          | H      | H     | $CHF_2$      | $CH_3$  |
| 21        | F  | $CH_2CN$                             | H      | H     | $CHF_2$      | $CH_3$  |
| 22        | F  | $CH_2CH_2CH_2F$                      | H      | H     | $CHF_2$      | $CH_3$  |
| 23        | F  | $CH_2CH_2CN$                         | H      | H     | $CHF_2$      | $CH_3$  |
| 24        | F  | $CH_2CH{=}CH-CH_3$                   | H      | H     | $CHF_2$      | $CH_3$  |
| 25        | F  | $CH(CH_3)CH_2CH_3$                   | H      | H     | $CHF_2$      | $CH_3$  |
| 26        | F  | $CH_2CH(CH_3)CH_2CH_3$               | H      | H     | $CHF_2$      | $CH_3$  |
| 27        | F  | $OCH_3$                              | H      | H     | $CHF_2$      | $CH_3$  |

TABLE 1-continued

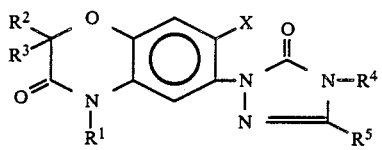

| Cmpd. No. | X | R$^1$ | R$^2$ | R$^3$ | R$^4$ | R$^5$ |
|---|---|---|---|---|---|---|
| 28 | F | OCH$_2$CH$_3$ | H | H | CHF$_2$ | CH$_3$ |
| 29 | F | CH$_2$SCH$_2$CH$_3$ | H | H | CHF$_2$ | CH$_3$ |
| 30 | F | CH$_2$C(CH$_3$)=CH$_2$ | H | H | CHF$_2$ | CH$_3$ |
| 31 | F | CH$_2$CH$_2$CH(CH$_3$)$_2$ | H | H | CHF$_2$ | CH$_3$ |
| 32 | F | CH$_2$(CH$_2$)$_3$CH$_3$ | H | H | CHF$_2$ | CH$_3$ |
| 33 | F | SO$_2$CH$_2$CH$_2$CH$_3$ | H | H | CHF$_2$ | CH$_3$ |
| 34 | F | CH$_2$C≡CI | H | H | CHF$_2$ | CH$_3$ |
| 35 | F | SO$_2$CH(CH$_3$)$_2$ | H | H | CHF$_2$ | CH$_3$ |
| 36 | F | CH$_2$CH=CH$_2$ | H | H | CHF$_2$ | CH$_3$ |
| 37 | F | CH$_2$C≡CH | H | CH$_3$ | CHF$_2$ | CH$_3$ |
| 38 | H | CH$_2$C≡CH | H | H | CHF$_2$ | CH$_3$ |
| 39 | H | CH$_2$CH=CH$_2$ | H | H | CHF$_2$ | CH$_3$ |
| 40 | F | CH$_2$CH=CH$_2$ | H | H | CH$_3$ | CHF$_2$ |
| 41 | H | H$_2$C\C=C/Cl, Cl/ \H | H | H | CHF$_2$ | CH$_3$ |
| 42 | H | H$_2$C\C=C/H, Cl/ \Cl | H | H | CHF$_2$ | CH$_3$ |
| 43 | F | H$_2$C\C=C/Cl, Cl/ \H | H | H | CHF$_2$ | CH$_3$ |
| 44 | F | H$_2$C\C=C/H, Cl/ \Cl | H | H | CHF$_2$ | CH$_3$ |
| 45 | H | CH$_2$C(Cl)=CH$_2$ | H | H | CHF$_2$ | CH$_3$ |
| 46 | F | CH$_2$C(Cl)=CH$_2$ | H | H | CHF$_2$ | CH$_3$ |
| 47 | F | CH$_2$CH=CHCH$_2$Cl | H | H | CHF$_2$ | CH$_3$ |
| 48 | H | CH$_2$CH=C(Cl)CH$_3$ | H | H | CHF$_2$ | CH$_3$ |
| 49 | F | CH$_2$CH=C(Cl)CH$_3$ | H | H | CHF$_2$ | CH$_3$ |
| 50 | H | CH$_2$CH=CHCl | H | H | CHF$_2$ | CH$_3$ |
| 51 | F | CH$_2$CH=CHCl | H | H | CHF$_2$ | CH$_3$ |
| 52 | H | CH$_2$CH=CCl$_2$ | H | H | CHF$_2$ | CH$_3$ |
| 53 | F | CH$_2$CH=CCl$_2$ | H | H | CHF$_2$ | CH$_3$ |
| 54 | H | CH$_2$C≡CBr | H | H | CHF$_2$ | CH$_3$ |
| 55 | F | CH$_2$C≡CBr | H | H | CHF$_2$ | CH$_3$ |
| 56 | F | CH$_2$C(Br)=CH$_2$ | H | H | CHF$_2$ | CH$_3$ |
| 57 | F | CH$_2$CHCH$_2$CH$_2$ | H | H | CHF$_2$ | CH$_3$ |
| 58 | F | H | H | H | CH$_3$ | CH$_3$ |
| 59 | F | CH$_2$CH$_2$CH$_3$ | H | H | CH$_3$ | H |

Other representative compounds are identical with compounds 1-10, 12-36, and 38-59 except that one of R$^2$ and R$^3$ is methyl.

Other representative compounds are identical with compounds 1-10, 12-36, and 38-59 except that one of R$^2$ and R$^3$ is methyl.

TABLE 2

| Cmpd. No. | Melting Point (°C.) | Empirical Formula | | Elemental Analysis | |
|---|---|---|---|---|---|
| | | | | C | H | N |
| 1 | oily solid | C$_{12}$H$_{19}$F$_3$N$_4$O$_3$ | C F | | | |
| 2 | oily solid | C$_{15}$H$_{15}$F$_3$N$_4$O$_3$ | C F | | | |
| 5 | glassy solid | C$_{15}$H$_{11}$F$_3$N$_4$O$_3$ | C F | 51.15 50.62 | 3.15 3.47 | 15.89 14.93 |
| 36 | light yellow | C$_{15}$H$_{13}$F$_3$N$_4$O$_3$ | C | 50.85 | 3.70 | 15.81 |

TABLE 2-continued

| Cmpd. No. | Melting Point (°C.) | Empirical Formula | | Elemental Analysis | | |
|---|---|---|---|---|---|---|
| | | | | C | H | N |
| | foam | | F | 50.56 | 4.00 | 15.55 |
| 37 | 123.5-125.5 | C$_{16}$H$_{13}$F$_3$N$_4$O$_3$ | C F | 52.47 51.77 | 3.67 3.29 | 16.11 14.19 |
| 56 | white foam | C$_{15}$H$_{22}$BrF$_3$N$_4$O$_3$ | C F | | | |
| 58 | 257-260(d) | C$_{11}$H$_{11}$FN$_4$O$_3$ | C F | 41.37 41.35 | 2.18 2.05 | 12.43 12.67 |
| 59 | 147-149 | C$_{14}$H$_{15}$FN$_4$O$_3$ | C F | | | |

TABLE 3

| | Preemergence Herbicidal Activity (% Control) | | | | | | | |
|---|---|---|---|---|---|---|---|---|
| | Compound | | | | | | | |
| | 1 | 2 | 5 | 36 | 37 | 56 | 58 | 59 |
| | Rate (kg/ha) | | | | | | | |
| Species | 0.5 | 0.0625 | 0.125 | 0.125 | 0.125 | 0.125 | 2.0 | 0.5 |
| Cotton | 100 | 100 | 100 | 100 | 100 | 40 | 0 | 0 |
| Soybean | 100 | 20 | 95 | 70 | 80 | 5 | 0 | 5 |
| Field Corn | 100 | 100 | 100 | 100 | 100 | 95 | 0 | 10 |
| Rice | 95 | 80 | 100 | 100 | 100 | 90 | 0 | 5 |
| Wheat | 100 | 100 | 100 | 100 | 95 | 80 | 5 | 10 |
| Morningglory | 100 | 100 | 100 | 100 | 100 | 80 | 0 | 20 |
| Wild Mustard | 100 | 100 | 100 | 100 | 100 | 100 | 0 | 10 |
| Velvetleaf | 100 | 100 | 100 | 100 | 100 | 95 | 0 | 0 |
| Barnyardgrass | 100 | 100 | 100 | 100 | 100 | 100 | 0 | 50 |
| Green Foxtail | 100 | 100 | 100 | 100 | 100 | 100 | 0 | 5 |
| Johnsongrass | 100 | 100 | 100 | 95 | 100 | 100 | 5 | 20 |

TABLE 4

| | Postemergence Herbicidal Activity (% Control) | | | | | | | |
|---|---|---|---|---|---|---|---|---|
| | Compound | | | | | | | |
| | 1 | 2 | 5 | 36 | 37 | 56 | 58 | 59 |
| | Rate (kg/ha) | | | | | | | |
| Species | 0.5 | 0.0625 | 0.125 | 0.125 | 0.125 | 0.125 | 2.0 | 0.5 |
| Cotton | 100 | 100 | 100 | 100 | 100 | 90 | 5 | 70 |
| Soybean | 100 | 90 | 100 | 90 | 90 | 70 | 10 | 60 |
| Field Corn | 100 | 100 | 100 | 100 | 100 | 90 | 5 | 50 |
| Rice | 95 | 80 | 100 | 100 | 95 | 80 | 10 | 5 |
| Wheat | 95 | 100 | 100 | 100 | 95 | 95 | 10 | 20 |
| Morningglory | 100 | 100 | 100 | 100 | 100 | 100 | 5 | 80 |
| Wild Mustard | 100 | 95 | 100 | 100 | 100 | 100 | 0 | 20 |
| Velvetleaf | 100 | 100 | 100 | 100 | 100 | 100 | 5 | 100 |
| Barnyardgrass | 100 | 100 | 100 | 100 | 100 | 100 | 5 | 30 |
| Green Foxtail | 100 | 100 | 100 | 100 | 100 | 100 | 20 | 30 |
| Johnsongrass | 80 | 100 | 100 | 100 | 100 | 70 | 0 | - |

It is apparent that various modifications may be made in the formulation and application of the compounds of this invention without departing from the inventive concepts herein as defined in the claims.

We claim:

1. Compound of the formula

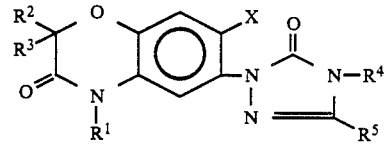

in which $R^1$ is H, alkyl, alkenyl, alkynyl, haloalkyl, haloalkenyl, haloalkynyl, alkoxyalkyl, alkoxyalkoxyalkyl, alkylsulfonyl, aralkyl, cycloalkyl, alkylthioalkyl, hydroxy or alkoxy;

$R^2$ and $R^3$ are independently H or alkyl;

X is H, Cl or F;

$R^4$ is alkyl, haloalkyl, alkenyl or alkynyl;

$R^5$ is alkyl or haloalkyl or H.

2. Compound of claim 1 in which $R^2$ and $R^3$ are H, X is F, $R^4$ is $CHF_2$ and $R^5$ is $CH_3$.

3. Compound of claim 2 in which $R^1$ is allyl.

4. Compound of claim 2 in which $R^1$ is propyl.

5. Compound of claim 2 in which $R^1$ is haloalkenyl.

6. Compound of claim 2 in which $R^1$ is propynyl.

7. An herbicidal composition comprising an herbicidally effective amount of the compound of claim 1 in admixture with a suitable carrier.

8. A method for controlling undesired plant growth which comprises applying to the locus where control is desired an herbicidally effective amount of the composition of claim 7.

9. An herbicidal composition comprising an herbicidally effective amount of the compound of claim 2 in admixture with a suitable carrier.

10. A method for controlling undesired plant growth which comprises applying to the locus where control is desired an herbicidally effective amount of the composition of claim 9.

* * * * *